(12) United States Patent
Nabel et al.

(10) Patent No.: US 6,884,431 B1
(45) Date of Patent: *Apr. 26, 2005

(54) METHOD FOR TREATING PROLIFERATIVE DISEASES WITH P27 AND FUSIONS THEREOF

(75) Inventors: Gary J. Nabel, Ann Arbor, MI (US); Elizabeth G. Nabel, Ann Arbor, MI (US)

(73) Assignee: The Regents of the University of Michigan, Ann Arbor, MI (US)

(*) Notice: Subject to any disclaimer, the term of this patent is extended or adjusted under 35 U.S.C. 154(b) by 122 days.

This patent is subject to a terminal disclaimer.

(21) Appl. No.: 09/708,276

(22) Filed: Nov. 7, 2000

Related U.S. Application Data

(63) Continuation of application No. 08/897,333, filed on Jul. 21, 1997, now Pat. No. 6,177,272.

(51) Int. Cl.[7] .................. A61K 48/00; C07H 21/04; C12N 15/86; A61M 25/10
(52) U.S. Cl. ............. 424/450; 424/93.1; 424/93.2; 424/93.6; 514/44; 435/320.1; 536/23.1; 536/23.2; 536/23.4; 604/508; 604/509; 604/96.01
(58) Field of Search .................. 424/450, 93.1, 424/93.2, 93.6; 514/44; 435/320.1; 536/23.1, 23.2, 23.4, 23.5; 604/508, 509, 96.01, 107

(56) References Cited

U.S. PATENT DOCUMENTS

| | | | | |
|---|---|---|---|---|
| 5,328,470 A | * | 7/1994 | Nabel et al. | ............... 604/101 |
| 5,672,508 A | * | 9/1997 | Gyuris et al. | ............ 435/320.1 |
| 5,688,665 A | | 11/1997 | Massague et al. | |
| 5,863,904 A | * | 1/1999 | Nabel et al. | ................ 514/44 |
| 5,962,424 A | * | 10/1999 | Hallahan et al. | ............. 514/44 |
| 6,110,744 A | * | 8/2000 | Fang et al. | ................ 435/456 |
| 6,218,372 B1 | * | 4/2001 | Nabel et al. | ................ 514/44 |
| 6,242,575 B1 | | 6/2001 | Massague et al. | |
| 6,316,208 B1 | | 11/2001 | Roberts et al. | |
| 6,355,774 B1 | | 3/2002 | Massague et al. | |
| 6,541,197 B2 | * | 4/2003 | Link, Jr. et al. | ................ 435/5 |

FOREIGN PATENT DOCUMENTS

| | | | | |
|---|---|---|---|---|
| WO | WO 95/18824 | | 7/1995 | |
| WO | WO 9602140 A1 | | 2/1996 | |
| WO | WO 96/25507 | * | 8/1996 | ............... 435/456 |

OTHER PUBLICATIONS

Craig et al. Proc. Annu. Meet. Assoc. Cancer Res. 37: A13 "Effects of a Recombinant Adenovirus Vector Expressing p27 on Cell Growth, Cell Cycle, Cyclin Kinases and Apoptosis".

PCT Notification of Transmission of The International Search Report or the Declaration (8 pages), Mailed Jan. 14, 1999.

Chen et al., "Downregulation of Cyclin–dependent Kinase 2 Activity and Cyclin A Promoter Activity in Vascular Smooth Muscle Cells by p27 $^{KIP1}$, an Inhibitor of Neointima Formation in the Rat Caroid Artery," pp. 2234–2341, J. Clin. Invest. 99 (10) 1997.

Toyoshima et al., "p27, a Novel Inhibitor of G1 Cyclin–Cdk Protein Kinase Activity, Is Related to p21," Cell, vol. 78, Jul. 15, 1994, pp. 67–74.

Tanner et al., "Expression of Cyclin–Dependent Kinase Inhibitors in Vascular Disease," pp. 396–403, Cir. Res. 1998; vol. 82.

Tanner et al., "Gene Transfer of p27 $^{KIP2}$ and p21 $^{CIP1}$ Cyclin–Dependent Kinase Inhibitors, But Not p16 $^{INX}$, Negatively Regulate VSMC Proliferation Through Differential Effects on Kinase Activity," Circulation vol. 96(8): SUPPL. p. 15 10/97.

Braun–Dullaeus et al., Regulation of Vascular Smooth Muscle Cell Proliferation by the Cyclin–Dependent Kinase Inhibitor p27 $^{KIP1}$, one page J. Invest. Med., vol. 45(3) p. 224A 3/97.

Hideo Toyoshima and Tony Hunter, "p27, a Novel Inhibitor of G1 Cyclin–Cdk Protein Kinase Activity, Is Related to p21", Cell, vol. 78, pp. 67–74, Jul. 15, 1994.

Kornelia Polyak et al., "Cloning of p27 $^{KIP1}$, a Cyclin–Dependent Kinase Inhibitor and a Potential Mediator of Extracellular Antimitogenic Signals", Cell, vol. 78, pp. 59–66, Jul. 15, 1994.

Steve Coats et al., "Requirement of p27 $^{KIP1}$ for Restriction Point Control of the Fibroblast Cell Cycle", Science, vol. 272, May 10, 1996, pp. 877–880.

Koyama et al. Fibrillarcollagen inhibits arterial smooth muscle proliferation through regulation of cdk2 inhibitors, Cell, vol. 87, 1069–1078, Dec. 13, 1996.

* cited by examiner

Primary Examiner—David Guzo
(74) Attorney, Agent, or Firm—Brinks Hofer Gilson & Lione

(57) ABSTRACT

The present invention is directed to a method of vascular proliferative disease by administering in vivo a gene encoding p27.

13 Claims, 7 Drawing Sheets

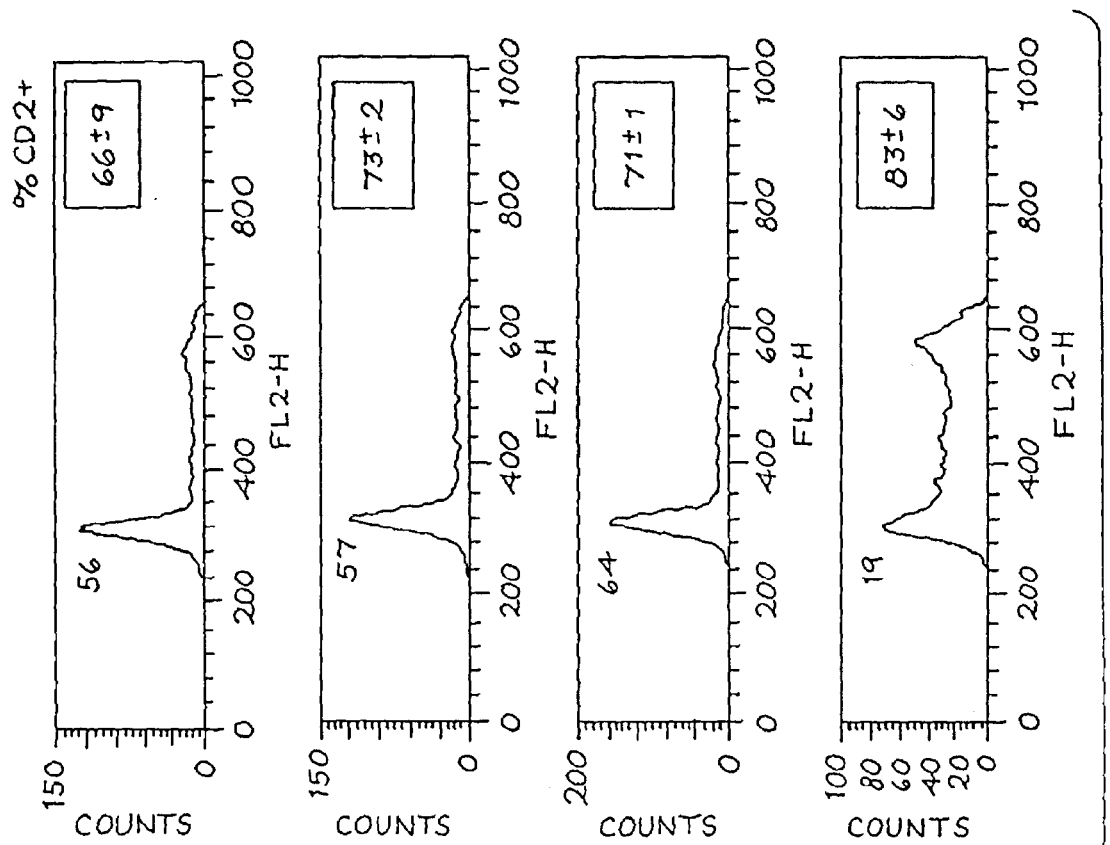
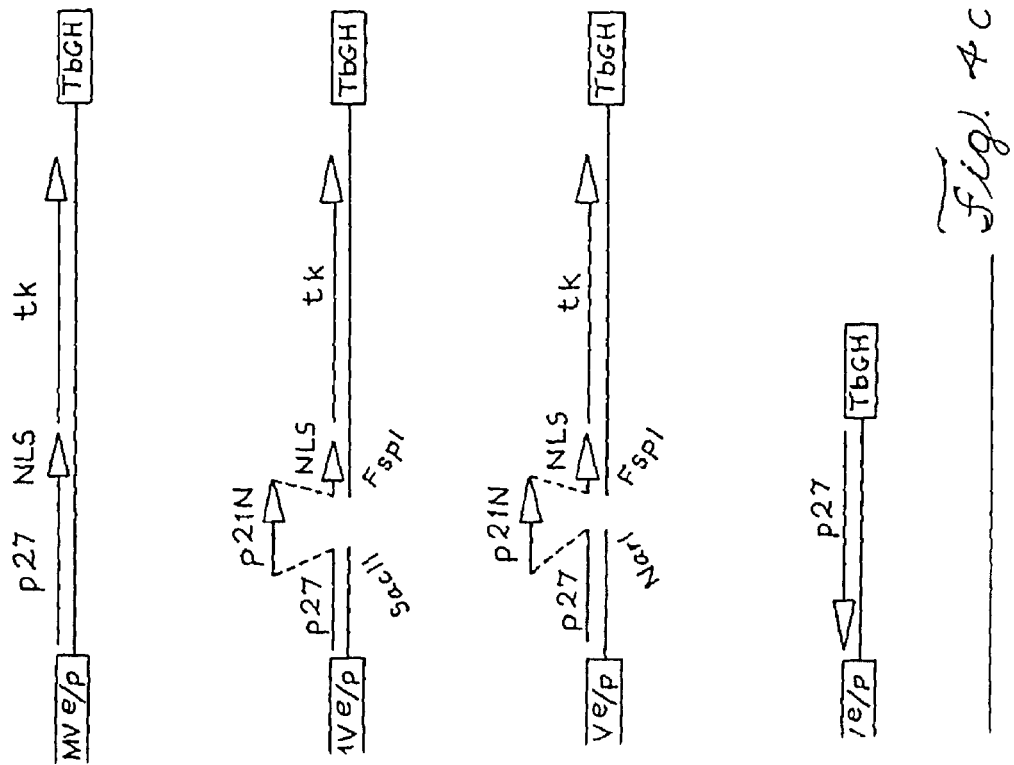
Fig. 4c

```
ATG TCA AAC GTG CGA GTG TCT AAC GGG AGC CCT AGC CTG GAG CGG ATG      48
Met Ser Asn Val Arg Val Ser Asn Gly Ser Pro Ser Leu Glu Arg Met
 1               5                  10                  15

GAC GCC AGG CAG GCG GAG CAC CCC AAG CCC TCG GCC TGC AGG AAC CTC      96
Asp Ala Arg Gln Ala Glu His Pro Lys Pro Ser Ala Cys Arg Asn Leu
             20                  25                  30

TTC GGC CCG GTG GAC CAC GAA GAG TTA ACC CGG GAC TTG GAG AAG CAC     144
Phe Gly Pro Val Asp His Glu Glu Leu Thr Arg Asp Leu Glu Lys His
         35                  40                  45

TGC AGA GAC ATG GAA GAG GCG AGC CAG CGC AAG TGG AAT TTC GAT TTT     192
Cys Arg Asp Met Glu Glu Ala Ser Gln Arg Lys Trp Asn Phe Asp Phe
     50                  55                  60

CAG AAT CAC AAA CCC CTA GAG GGC AAG TAC GAG TGG CAA GAG GTG GAG     240
Gln Asn His Lys Pro Leu Glu Gly Lys Tyr Glu Trp Gln Glu Val Glu
 65                  70                  75                  80

AAG GGC AGC TTG CCC GAG TTC TAC TAC AGA CCC CCG CGG CCC CCC AAA     288
Lys Gly Ser Leu Pro Glu Phe Tyr Tyr Arg Pro Pro Arg Pro Pro Lys
                 85                  90                  95

GGT GCC TGC AAG GTG CCG GCG CAG GAG AGC CAG GAT GTC AGC GGG AGC     336
Gly Ala Cys Lys Val Pro Ala Gln Glu Ser Gln Asp Val Ser Gly Ser
             100                 105                 110

CGC CCG GCG GCG CCT TTA ATT GGG GCT CCG GCT AAC TCT GAG GAC ACG     384
Arg Pro Ala Ala Pro Leu Ile Gly Ala Pro Ala Asn Ser Glu Asp Thr
         115                 120                 125

CAT TTG GTG GAC CCA AAG ACT GAT CCG TCG GAC AGC CAG ACG GGG TTA     432
His Leu Val Asp Pro Lys Thr Asp Pro Ser Asp Ser Gln Thr Gly Leu
 130                 135                 140

GCG GAG CAA TGC GCA GGA ATA AGG AAG CGA CCT GCA ACC GAC GAT TCT     480
Ala Glu Gln Cys Ala Gly Ile Arg Lys Arg Pro Ala Thr Asp Asp Ser
145                 150                 155                 160

TCT ACT CAA AAC AAA AGA GCC AAC AGA ACA GAA GAA AAT GTT TCA GAC     528
Ser Thr Gln Asn Lys Arg Ala Asn Arg Thr Glu Glu Asn Val Ser Asp
                 165                 170                 175

GGT TCC CCA AAT GCC GGT TCT GTG GAG CAG ACG CCC AAG AAG CCT GGC     576
Gly Ser Pro Asn Ala Gly Ser Val Glu Gln Thr Pro Lys Lys Pro Gly
             180                 185                 190

CTC AGA AGA CGT CAA ACG TAA                                         597
Leu Arg Arg Arg Gln Thr
         195
```

Fig. 5

SEQUENCE LISTING

<160> NUMBER OF SEQ ID NOS: 9

<210> SEQ ID NO 1
<211> LENGTH: 597
<212> TYPE: DNA
<213> ORGANISM: Homo sapiens

<400> SEQUENCE: 1

```
atgtcaaacg tgcgagtgtc taacgggagc cctagcctgg agcggatgga cgccaggcag      60
gcggagcacc ccaagccctc ggcctgcagg aacctcttcg gcccggtgga ccacgaagag     120
ttaacccggg acttggagaa gcactgcaga gacatggaag aggcgagcca gcgcaagtgg     180
aatttcgatt ttcagaatca caaaccccta gagggcaagt acgagtggca agaggtggag     240
aagggcagct tgcccgagtt ctactacaga ccccgcggc cccccaaagg tgcctgcaag      300
gtgccggcgc aggagagcca ggatgtcagc gggagccgcc cggcggcgcc tttaattggg     360
gctccggcta actctgagga cacgcatttg gtggacccaa agactgatcc gtcggacagc     420
cagacggggt tagcggagca atgcgcagga ataaggaagc gacctgcaac cgacgattct     480
tctactcaaa acaaaagagc caacagaaca gaagaaaatg tttcagacgg ttccccaaat     540
gccggttctg tggagcagac gcccaagaag cctggcctca gaagacgtca aacgtaa       597
```

<210> SEQ ID NO 2
<211> LENGTH: 198
<212> TYPE: PRT
<213> ORGANISM: Homo sapiens

<400> SEQUENCE: 2

```
Met Ser Asn Val Arg Val Ser Asn Gly Ser Pro Ser Leu Glu Arg Met
 1               5                  10                  15

Asp Ala Arg Gln Ala Glu His Pro Lys Pro Ser Ala Cys Arg Asn Leu
            20                  25                  30
```

-continued

```
Phe Gly Pro Val Asp His Glu Glu Leu Thr Arg Asp Leu Glu Lys His
         35                  40                  45

Cys Arg Asp Met Glu Glu Ala Ser Gln Arg Lys Trp Asn Phe Asp Phe
 50                  55                  60

Gln Asn His Lys Pro Leu Glu Gly Lys Tyr Glu Trp Gln Glu Val Glu
 65                  70                  75                  80

Lys Gly Ser Leu Pro Glu Phe Tyr Tyr Arg Pro Pro Arg Pro Pro Lys
                 85                  90                  95

Gly Ala Cys Lys Val Pro Ala Gln Glu Ser Gln Asp Val Ser Gly Ser
            100                 105                 110

Arg Pro Ala Ala Pro Leu Ile Gly Ala Pro Ala Asn Ser Glu Asp Thr
        115                 120                 125

His Leu Val Asp Pro Lys Thr Asp Pro Ser Asp Ser Gln Thr Gly Leu
    130                 135                 140

Ala Glu Gln Cys Ala Gly Ile Arg Lys Arg Pro Ala Thr Asp Asp Ser
145                 150                 155                 160

Ser Thr Gln Asn Lys Arg Ala Asn Arg Thr Glu Glu Asn Val Ser Asp
                165                 170                 175

Gly Ser Pro Asn Ala Gly Ser Val Glu Gln Thr Pro Lys Lys Pro Gly
            180                 185                 190

Leu Arg Arg Arg Gln Thr
        195
```

<210> SEQ ID NO 3
<211> LENGTH: 4
<212> TYPE: PRT
<213> ORGANISM: Homo sapiens

<400> SEQUENCE: 3

Arg Arg Gln Thr
 1

<210> SEQ ID NO 4
<211> LENGTH: 4
<212> TYPE: PRT
<213> ORGANISM: Homo sapiens

<400> SEQUENCE: 4

Thr Pro Lys Lys
 1

<210> SEQ ID NO 5
<211> LENGTH: 4
<212> TYPE: PRT
<213> ORGANISM: Homo sapiens

<400> SEQUENCE: 5

Ala Ala Gly Gly
 1

<210> SEQ ID NO 6
<211> LENGTH: 23
<212> TYPE: DNA
<213> ORGANISM: Homo sapiens

<400> SEQUENCE: 6
cgattttcag aatcacaaac ccc                                           23

<210> SEQ ID NO 7
<211> LENGTH: 33

-continued

```
<212> TYPE: DNA
<213> ORGANISM: Homo sapiens

<400> SEQUENCE: 7
gccaggcccc ccggccgcct gctccacaga acc                          33

<210> SEQ ID NO 8
<211> LENGTH: 32
<212> TYPE: DNA
<213> ORGANISM: Homo sapiens

<400> SEQUENCE: 8
gagcaggcgg ccggggggcc tggcctcaga ag                           32

<210> SEQ ID NO 9
<211> LENGTH: 21
<212> TYPE: DNA
<213> ORGANISM: Homo sapiens

<400> SEQUENCE: 9
tttggccgca gaggcacctg t                                       21
```

METHOD FOR TREATING PROLIFERATIVE DISEASES WITH P27 AND FUSIONS THEREOF

This application is a continuation of U.S. Ser. No. 08/897,333, filed Jul. 21, 1997, now U.S. Pat. No. 6,177,272, herein incorporated by reference in its entirety.

BACKGROUND OF THE INVENTION

1. Field of the Invention

The present invention provides methods for treating or preventing vascular proliferative diseases in vivo by administration of a gene which encodes p27.

2. Discussion of the Background

Vascular diseases are characterized by a fibroproliferative response to injury consisting of smooth muscle cell proliferation and migration as well as connective tissue formation. The mechanisms by which vascular smooth muscle cells (VSMC) proliferate in response to mitogenic signals are well described; however, the role of cellular gene products which cause VSMC to shift from a proliferative to a non-proliferative state during G1 phase of the cell cycle are not well understood.

It is known that transitions between phases of the cell cycle are catalyzed by a family of cyclin-dependent kinases (P. Nurs, (1990) Nature 344, 503–508; L. Hartwell et al., (1974) Science 183 46–51). In many cells, transit through G1 of the cell cycle and entry into S phase requires a binding and activation of cyclin/cyclin-dependent kinase complexes (CDK), predominantly cyclin D-cdk4,6 and cyclin E-cdk2 (C. J. Sherr, (1994) Cell 79, 551; C. J. Sherr (1996) Science 274, 1672).

The cyclin-dependent kinase inhibitors (CKIs) are naturally-occurring gene products which inhibits cyclin-CDK activity and phosphorylation of retinoblastoma (Rb), resulting in G1/S growth arrest (D. O. Morgan, Nature 1995, 374: 171; C. J. Sherr & J. M. Roberts, Genes. Dev. 1995, 9: 1149). CKIs directly implicated in CDK regulation are p21$^{cip1/Waf1}$ (Y. Xiong, et al., Nature 1993, 366: 701; J. W. Harper et al., Cell 1993, 75: 805), p27$^{Kip1}$ (H. Pyoshima, T. Hunter, Cell 1994, 78: 67; K. Polyak et al., Cell 1994, 78: 59; S. Coats et al., Science 1996, 272; 877), and p16/p15$^{INKN}$ (M. Serrano et al., Nature 1993, 366: 704).

Previous studies of these CKIs were focused on their potential role in malignant transformation. For example, PCT Publication No. WO95/18824 (applicant Sloan-Kettering Institute For Cancer Research) describes a method for identifying agents capable of modulating the ability of p27 to inhibit the activation of the cyclin E-Cdk2 complex. This PCT publication further provides methods for treating subjects diagnosed with a hyperproliferative disorder, such as cancer and hyperplasia, using these agents. Such agents can be both protein and non-protein moieties. Unfortunately, the involvement of CKIs in cardiovascular diseases, including atherosclerosis, angiogenesis and restenosis, has not been well studied.

There are currently a number of methods used to treat cardiovascular diseases which focus on inhibiting cell proliferation. The main problems associated with the available therapies revolve around targeting the inhibitory agent to the proliferating cells that need to be killed. Targeting has traditionally been attempted using chemo- or radiotherapeutic agents coupled with antibodies. More recently, gene therapy approaches have been used that target proliferating cells by providing gene products detrimental to specific cell types. The genes encoding these gene products are known as suicide genes. The gene products are either instilled site specifically, expressed in specific cells using vectors which target specific cells or expressed under the control of a cell type-specific promoter.

The HSV-1 thymidine kinase gene (TK) is the most widely used suicide gene in mammalian systems. TK efficiently phosphorylates guanosine analogs ganciclovir (GCV) and acyclovir (ACV), which are subsequently phosphorylated by cellular enzymes into their triphosphate forms. These end-products are incorporated into the growing DNA chain, leading to elongation arrest (ACV) or a drastic slow down in DNA synthesis (GCV). Death usually ensues, through a mechanism identified in some cell lines as apoptosis. The mechanism that triggers cell death is not known. In the case of GCV, another action other than at the level of the DNA polymerase inhibition might exist, since no correlation is observed between the inhibition of mutant viral DNA polymerase by GCV and growth of these mutants in the presence of GCV.

One of the peculiar features of the TK-GCV system is the bystander effect that characterized the death of untransduced cells. Two mechanisms have been proposed to explain this phenomenon. In 1993, Freeman and colleagues hypothesized that the uptake of phosphorylated GCV by bystander cells occurs via the endocytosis of apoptotic vesicles, originating from the TK-transduced cells, and containing the toxic drug. However increasing evidence suggests that the bystander effect is mediated via gap junctional intercellular communications, that allow phosphorylated ganciclovir to translocate from TK$^+$ to TK$^-$ cells. In 1995, using a flow cytometry assay to quantitate cellar coupling, Fick and colleagues found that bystander tumor cytotoxicity during GCV treatment was highly correlated with the exent of gap junction-mediated coupling. In a TK-expressing neuro-2a murine neuroblastoma cell line, which do not normally exhibit any bystander effect, adenovirus-mediated overexpression of connexin-43 was shown to confer bystander effect-mediated cell killing.

The TK-GCV system has already been successfully applied in cancer models as well as restenosis in vivo (Plautz et al., Circulation 1991, 83:578; Ohno et al., Science 1994, 265:781). However, the efficiency of gene delivery in vivo remains very low, and enhancement of TK-mediated killing at other levels must be considered. In an attempt to link TK-mediated tumor suppression and immune system, retroviral vectors were constructed carrying both the HSV-TK and interleukin-2 genes. However, using a rat 9L gliosarcoma model, no enhancement of tumor eradication was observed with this vector.

SUMMARY OF THE INVENTION

Accordingly, one object of the present invention is to provide methods for treating and preventing vascular proliferative diseases in vivo.

In one application, the present invention provides a method for treating and preventing restenosis in vivo.

In a second application, the present invention provides a method for treating and preventing atherosclerosis in vivo.

In a third application, the present invention provides a method for treating and preventing angiogenesis in vivo.

The present inventors have now found that p27 functions in arteries to control the response to acute injury and cell proliferation. The present inventors provide the first direct demonstration that p27 expression and overexpression is sufficient to produce inhibition of vascular smooth muscle cell growth in vivo. Therefore, the present invention relates to the use of the p27 gene as an anti-proliferative gene to treat vascular proliferative diseases including coronary and peripheral restenosis.

The methods described herein are aimed at increasing the bystander effect. Since the mechanism of action of TK is likely to be at the level of DNA replication, arresting proliferating cells makes them transiently insensitive to TK-GCV mediated killing, prolongs their life and the duration of TK expression, thereby increases the translocation of phosphorylated GCV to bystander cells.

BRIEF DESCRIPTION OF THE FIGURES

FIG. 2A is a schematic representation of the constructs expressing p27 and TK. FIG. 2B is a histogram demonstrating the DNA profile of 293 cells transfected with the above-described plasmids and a CD2-expressing plasmid. All the CD-2 expressing cells are included in the analysis. The fraction of cells in each phase of the cell cycle is indicated above the corresponding peak. The percentages of CD-2-positive cells are indicated in the upper right corner of each graph to illustrate the variability in transfection efficiency. FIG. 2C is a graph showing the growth of 293 cells transfected with the above-described plasmids in the presence or in the absence of 5 µM GCV. Proliferation was measured using a colorimetric assay. Data is the average of 3 measurements.

FIG. 3B is a histogram demonstrating the DNA profile of 293 cells transfected with the above-described plasmids and a CD2-expressing plasmid. The fraction of cells in G1 phase of the cell cycle is indicated above the corresponding peak. The percentages of CD-2-positive cells are indicated the upper right corner of each graph to illustrate the variability in transfection efficiency. All values are the average of two experiments FIG. 3C demonstrates the bystander assay. Renca cells were transfected with the various plasmids and diluted with untransfected cells. Addition of 5 µM GCV to the culture medium and cell proliferation assay were performed 1 and 5 days post-transfection, respectively.

FIGS. 4A–C. FIG. 4A is a histogram showing that mutation of the cdc2 kinase consensus site TRKK into GGAA moderately increase p27 activity. FIG. 4B is a histogram showing the internal deletions inside the p27 coding region increase p27 activity. FIG. 4C shows that fusion of the N-terminal domains of p21 and p27 does not increase cell cycle arrest in G1. All experiments were preformed using 293 cells as in FIGS. 2B and 3B.

FIG. 5 illustrates the DNA and protein sequences of p27 (SEQ ID NOs: 1–2).

DETAILED DESCRIPTION OF THE EMBODIMENTS

Figure 1:
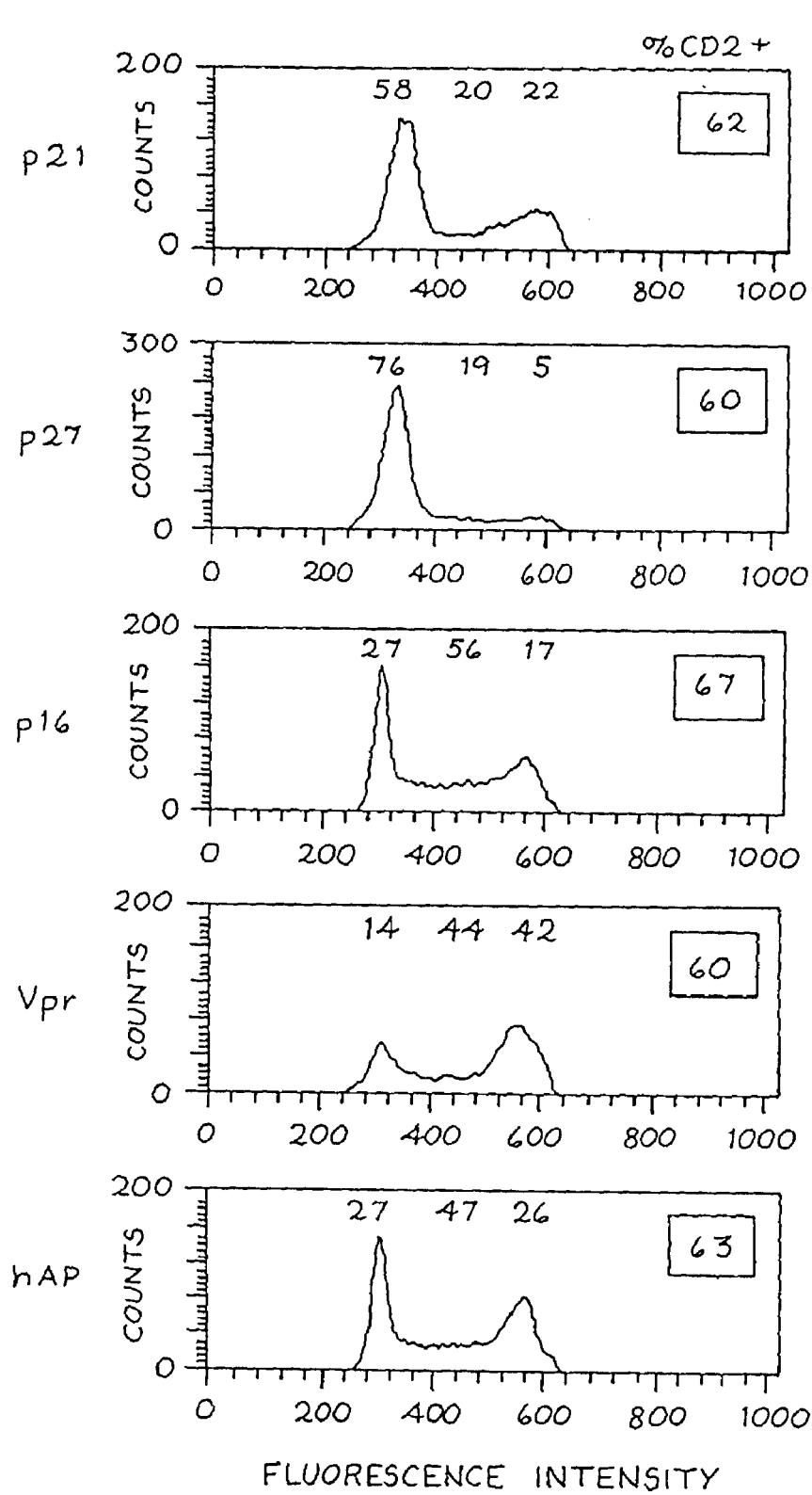
FIG. 1 are histograms represent the DNA profile of the 293 cells transformed with (i) vectors expressing p21, p27, p16, Vpr or hAP under the control of CMV enhancer/promoter and (ii) a CD-2 expressing plasmid. The fraction of cells in each phase of the cell cycle is indicated above the corresponding peak. The percentage of DNA-positive cells are indicated in the upper right corner of each graph to illustrate the variability in transfection efficiency.
Figure 2:
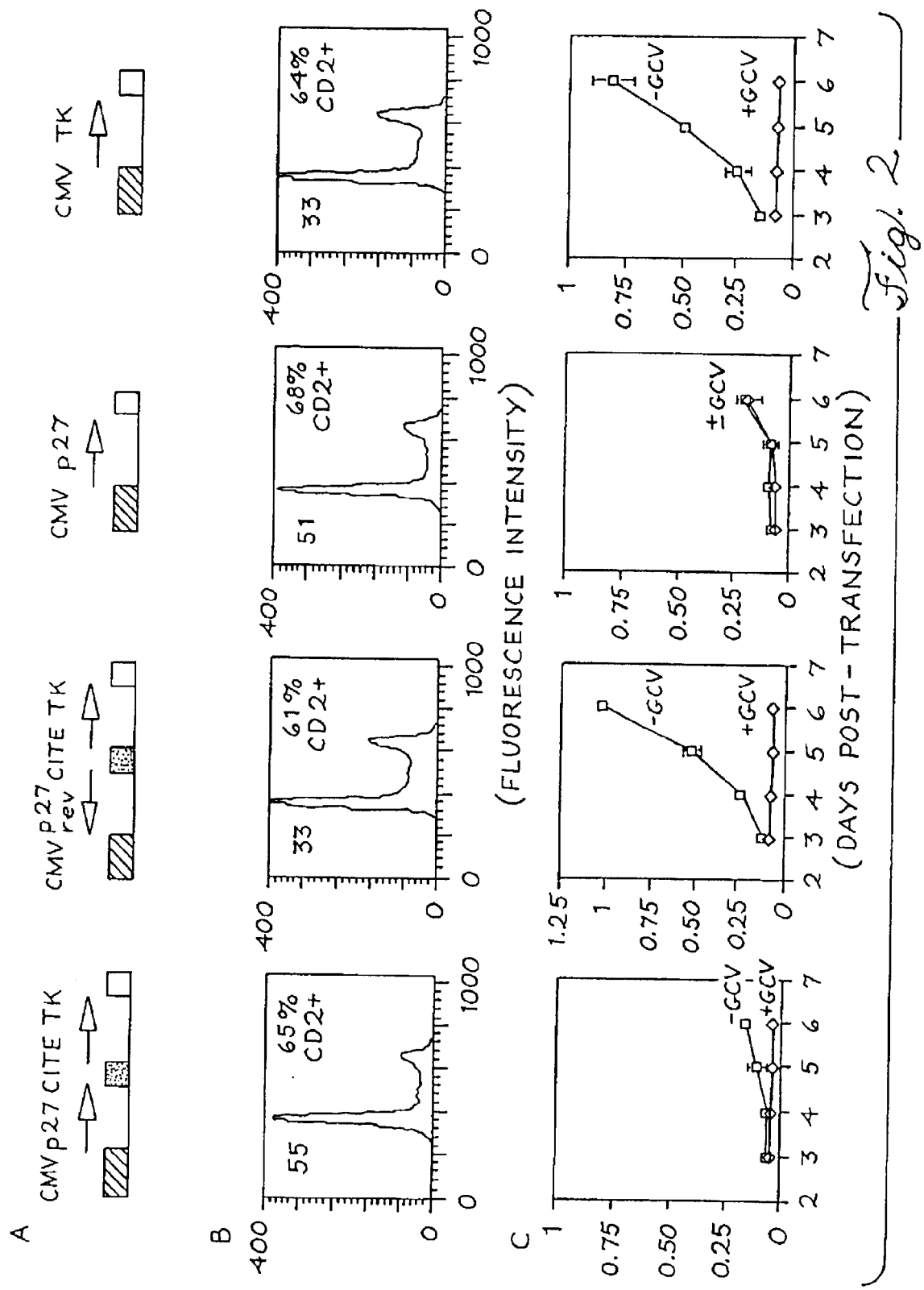
FIGS. 2A–C.
Figure 3:
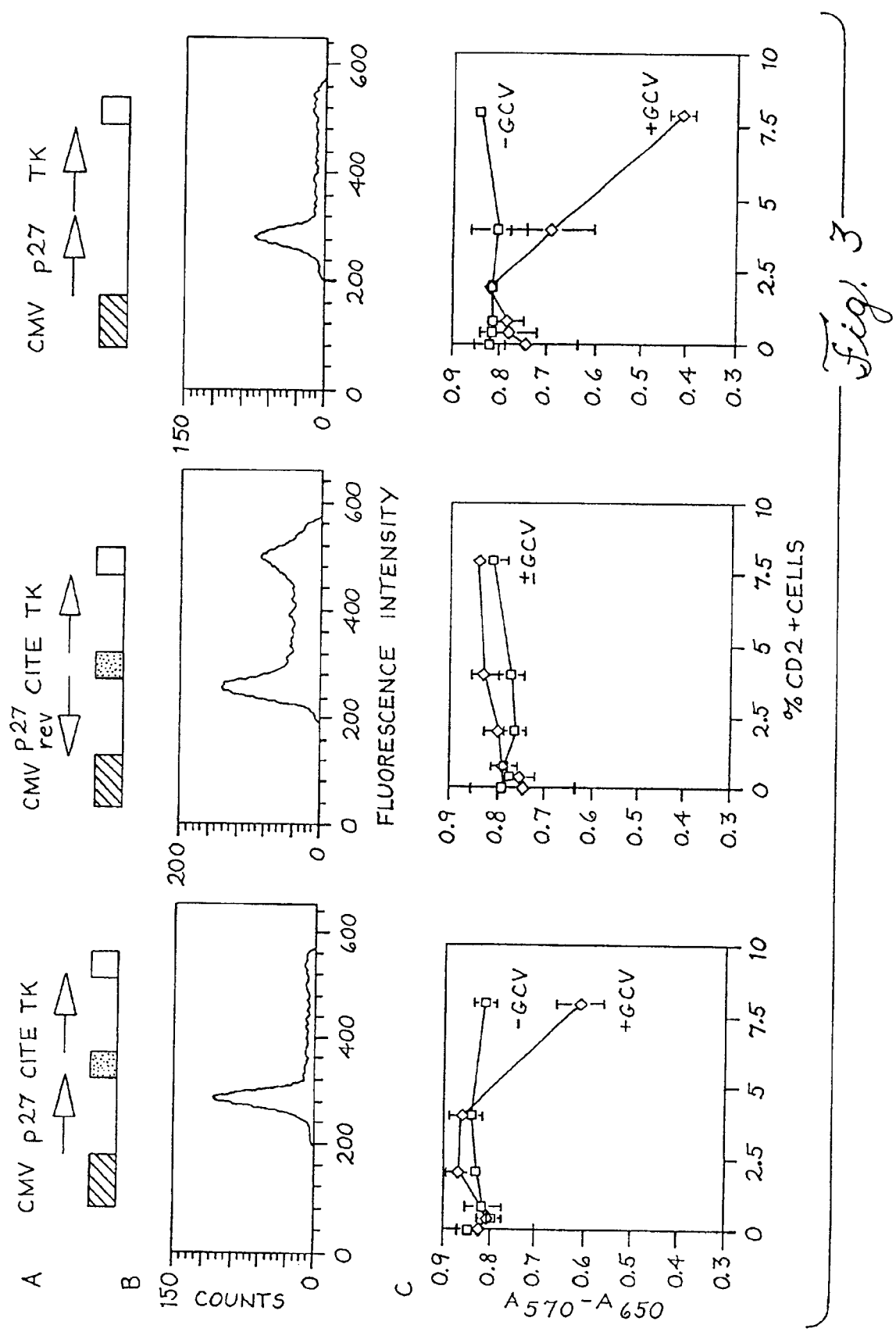
FIGS. 3A–C FIG. 3A is a schematic representation of the constructs expressing p27 and TK.
Figure 4A:
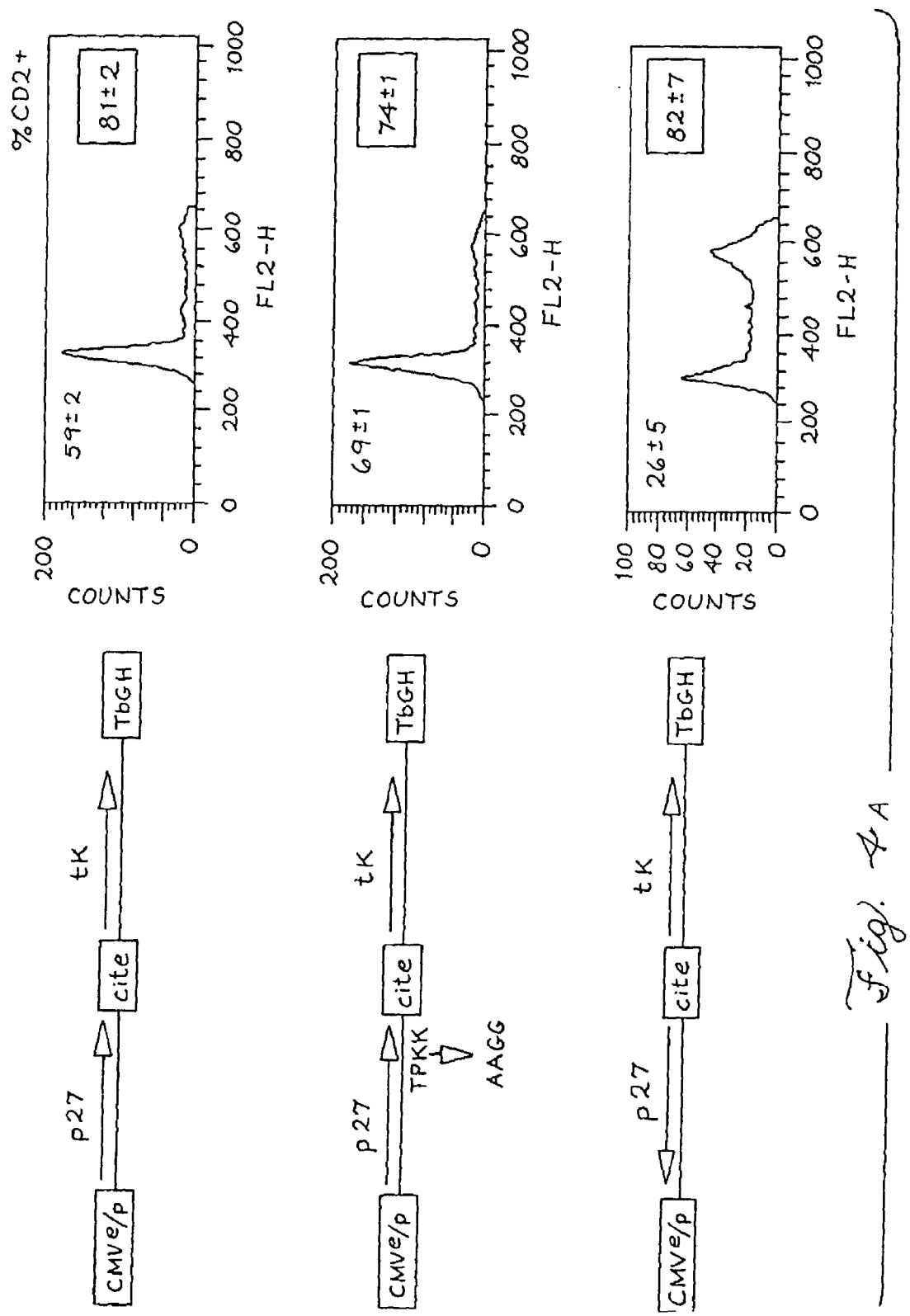
Figure 4B:
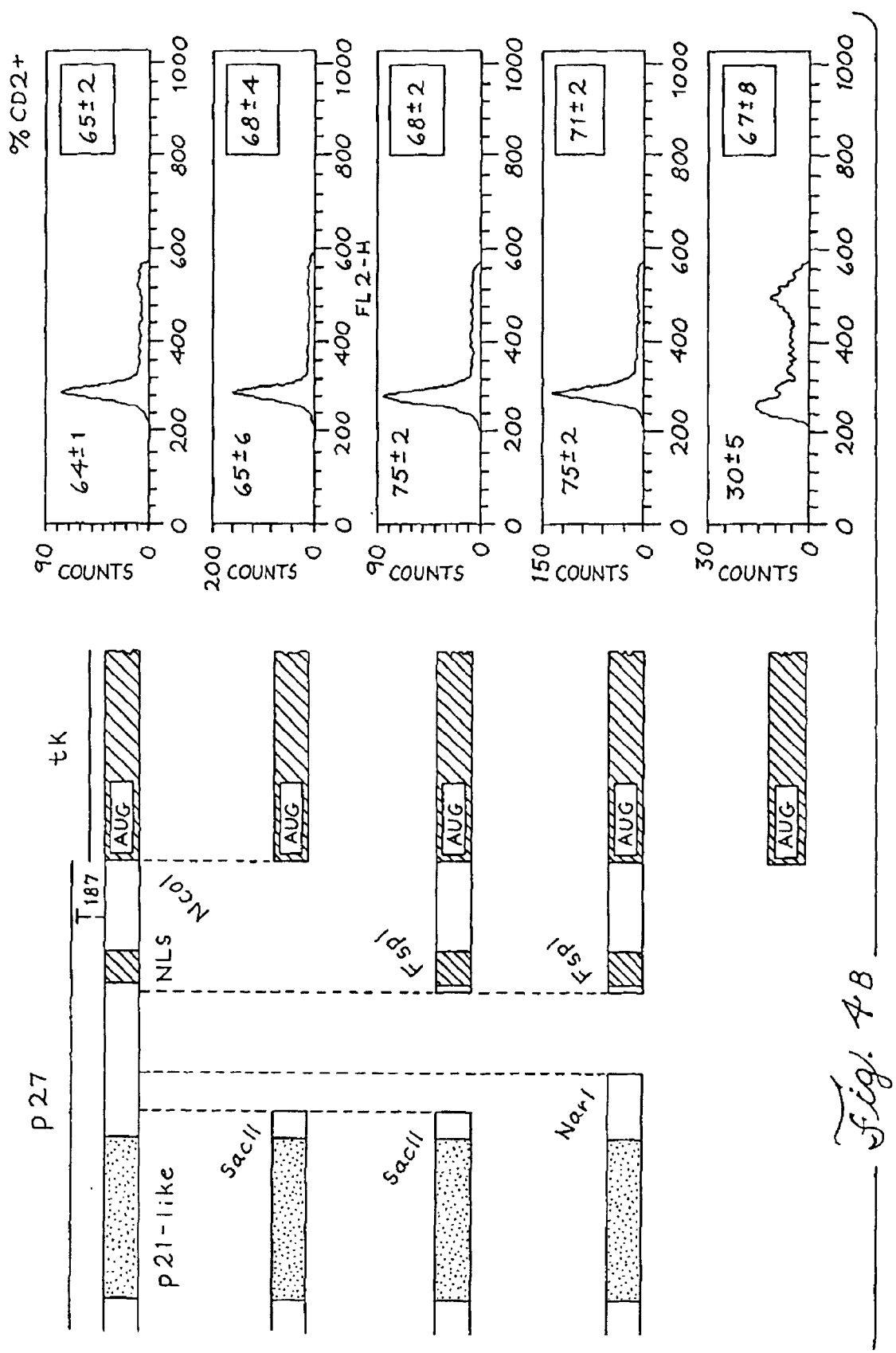

The present invention provides a method for treating vascular proliferative diseases comprising administering to a patient in need thereof a therapeutically effective amount of a gene which encodes p27 or a fusion protein thereof.

I. p27 And Fusion Proteins Thereof

The amino acid sequence of p27 (the first polypeptide) is shown in FIG. 5 (SEQ ID NO:2). Any DNA which encodes this protein can be used in accordance with the present invention. cDNAs encoding p27 are described by PCT Publication No. WO95/18824, PCT Publication WO 96/02140 (Applicant: Sloan-Kettering Institute For Cancer Research), Toyoshima et al. (*Cell* 1994, 78:67–74) and Polyak et al. (*Cell* 1994, 78:59–66). As used hereinafter, "p27" refers both to native p27 as well as mutated p27 and fusion proteins thereof.

The term "mutated p27" includes polypeptides having an amino acid sequence which is similar to a wild-type p27 but which has at least one amino acid different from wild-type p27. The amino acid difference(s) between a mutated p27 and a wild-type p27 may be substitution of one or more amino acids, deletion of one or more amino acids or addition of one or more amino acids. Preferred sites for mutations include the last four carboxy terminal amino acid residues or the last twelve basepairs at the 3' terminus of the DNA encoding the protein. Preferably, the basepairs are manipulated so as to introduce a restriction endonuclease site at that terminus of the DNA.

In an alternate embodiment, p27 is operatively linked to a second polypeptide which directly or indirectly activates transcription in eukaryotic cells. To operatively link the first and second polypeptides, typically nucleotide sequences encoding the first and second polypeptides are ligated to each other in-frame to create a chimeric gene encoding a fusion protein, although the first and second polypeptides can be operatively linked by other means that preserve the function of each polypeptide (e g., chemically crosslinked).

The second polypeptide can be selected from the group consisting of HSV thymidine kinase (McKnight, *Nucleic Acids Res.* 1980, 8:5949; Mansour et al., *Nature* 1988, 336:348–352), β-galactosidase, p16 (Chan et al., *Mol. Cell. Biol.* 1995, 15:2682–2688; Guan et al., *Genes & Dev.* 1994, 8:2939–2952), p21 (Harper et al., *Cell* 1993, 75:805; Xiong et al., *Nature* 1993, 366:701, p57 (Lee et al., *Genes & Dev.* 1995, 9:639–649; Matsuoka et al., *Genes & Dev.* 1995, 2:650–662), retinoblastoma (Rb) (see Chang et al., *Science* 1995, 267:518) or its mutants (see for example, Hamel et al., *Mol. Cell. Biol.* 1992, 12:3431), cytosine deaminase (WO 9428143; Wang et al., *Can. Soc. Petrol. Geol. Mem.* 1988, 14:71), nitric oxide, and nitric oxide synthetase.

II. Expression Systems

Suitable expression vectors useful in accordance with the present invention include eukaryotic and viral vectors. Useful eukaryotic vectors include pRcRSV and pRcCMV. Preferably, viral vectors are used.

Viral vector systems have been indicated as highly efficient in transferring genes to mammals containing deficient genes. See, for example, Crystal, *Am. J. Med.* 1992, 92(6A): 44S–52S; Lemarchand et al. *Proc. Nat'l Acad Sci. USA* 1992, 89(14):6482–6486. Preferably, retroviral vectors with impaired ability to replicate and transform are used. Suitable viral vectors which express p27 useful in accordance with the present invention include adenoviral vectors, Ad5-360 in combination with pAd-BghVI as described by Davidson et al., *Nature Gen* 1993, 3:219. Preferably, adenoviral vectors are used.

Preferably, adenoviral vectors include: ADV described by Davidson et al., *Nature Gen.* 1993, 3:219; or other adenovirus types, including types 7001, or types 1 or 12 (as described by Yang et al., *Nat. Med.* 1995, 1:1052 and Ohno et al., *Science* 1994, 265:781).

The p27 can be inserted into these expression vectors and used for cell transfection using conventional recombinant techniques such as described by Sambrook, Fritsch, & Maniatis, in "Molecular Cloning, A Laboratory Manual" (2d ed): pp. E5. (Cold Spring Harbor Press, Cold Spring Harbor, N.Y., 1989), the disclosure of which is hereby incorporated by reference. Alternatively, the expression vectors can be prepared using homologous recombination techniques as described by Davidson et al., Nature Gen. 1993, 3:219–223 or Lemarchand et al., Proc. Nat'l Acad. Sci. USA 1992, 89 (14):6482–6486.

The expression vectors of the present invention can additionally contain regulatory elements such as promoters, and enhancers and selection markers such as antibiotic resistance genes.

Additionally, the expression vectors of the present invention can contain other therapeutically useful genes under control of the same regulatory elements as p27 or under independent regulation.

It is well established that viral vectors are taken up in and integrated into cells in vivo and express their DNA, including any inserted constructs. See, e.g., Yoshimura et al., J. Biol. Chem. 1993, 268 (4):2300–2303; Crystal, Am. J. Med. 1992, 92(6A):445–525; Lemarchand et al., Proc. Nat'l Acad. Sci. USA 1992, 89(14):6484–6486; the disclosures of which are hereby incorporated by reference.

In an alternate embodiment, it is also understood that other delivery systems besides expression vectors can be used to deliver p27 protein. Principally, these techniques, including the use of liposomes and DNA conjugates, are expected to provide similar delivery yields as those provided by the expression vectors discussed above. That is, rather than expressing the p27 gene via an expression vector, it is also possible to incorporate a therapeutic amount of a gene encoding p27 in a liposome.

In addition, combination therapies of viral vectors and liposomes have also shown tremendous promise and are also contemplated for use in the invention. Yoshimura et al., J. Biol. Chem. 1993, 268(4):2300–2303.

Liposomes are known to provide highly effective delivery of active agents to diseased tissues. For example, pharmacological or other biologically active agents have been effectively incorporated into liposomes and delivered to cells. Thus, constructs in accordance with the present invention can also be suitably formed in liposomes and delivered to selected tissues. Liposomes prepared from cationic lipids, such as those available under the trademark LIPOFECTIN (Life Technologies, Inc., Bethesda, Md.) are preferred. Particularly appealing to liposome based treatments is the fact that liposomes are relatively stable and possess relatively long lives, prior to their passage from the system or their metabolism. Moreover, liposome do not raise major immune responses.

Thus, in one aspect of the present invention a vector containing a gene encoding p27 is incorporated into a liposome and used for the delivery of the construct to a specific tissue. The liposome will aid the construct in transfecting a cell and becoming expressed by the cell, ultimately generating p27 protein.

III. Therapeutic compositions

The composition of the present invention is a therapeutically effective amount of a gene which expresses p27 and a pharmaceutically acceptable carrier. In order to administer the gene, suitable vectors and carriers may be incorporated into the formulations to provide improved expression of p27.

Any of the foregoing formulations may be appropriate in the treatment with the viral vectors, provided that the viral particles are inactivated in the formulation and the formulation is physiologically compatible.

The amount of p27 to be administered will depend on the size of the patient and the state to which the disease has progressed. By modifying the regulatory elements of the gene using conventional recombinant DNA techniques or by varying the amount of gene titer administered, the amount of p27 expression can be adjusted to the patient's needs. Typically, it is desirable to deliver approximately 50 viral vectors per cell to be treated. With the adenovirus, formulations should generally contain on the order of $10^{10}$ viral infectious units per ml. With retrovirus, slightly different titers may be applicable. See Woo et al., Enzyme 1987, 38:207–213. Additional assistance in determining appropriate dosage levels can be found in Kay et al., Hum. Gene Ther. 1992, 3:641–647; Liu et al., Somat. Cell Molec. Genet. 1992, 18:89–96; and Ledley et al., Hum. Gene Ther. 1991, 2:331–358.

Depending upon the particular formulation that is prepared for the administration of the expression vectors, administration of the compositions of the present invention can be accomplished through a variety of methods. The composition of the present invention are preferably administered by direct injection of the expression vector (or liposome containing the same) into the tissue or by balloon catheter implantation into the blood vessel wall, such as described in U.S. Pat. No. 5,328,470. In a less preferred embodiment, cells from a patient can be collected, transformed with p27 in vitro and replaced in the patient.

IV. Applications of the Invention

The invention may be particularly useful for gene therapy purposes, in treatments for vascular proliferative diseases. The general approach of gene therapy involves the introduction of nucleic acid into cells such that one or more gene products encoded by the introduced genetic material are produced in the cells to restore or enhance a functional activity. For reviews on gene therapy approaches see W. F. Anderson, Science 1992, 256:808–813; A. D. Miller, Nature 1992, 357:455460; Friedmann, T., Science 1989, 244:1275–1281; and D. Cournoyer et al., Curr. Opin. Biotech. 1990, 1:196–208.

Vascular proliferative diseases that can be treated by the methods of the present invention are characterized by intimal smooth muscle cell growth in response to vascular injury. Examples of vascular proliferative diseases include atherosclerosis, angiogenesis, and restenosis.

Atherosclerosis is an atherosclerosis characterized by irregularly distributed lipid deposits in the intima of large and medium-sized arteries. Atherosclerosis is a multi-stage process set in motion when cells lining the arteries are damages as a result of high blood pressure, smoking, toxic substances in the environment, and other agents. The disease is characterized by plaque build-up when high density lipoproteins accumulate at the site of arterial damage and platelets act to form a fibrous cap over this fatty core.

Angiogenesis is the development of new blood vessels.

Arterial injury from angioplasty induces a series of proliferative, vasoactive, and inflammatory responses which can lead to restenosis. Although several factors have been defined which stimulate this process in vivo, the role of specific cellular gene products in limiting the response is not well understood. The present inventors have now found that p27 acts to limit the proliferative response to balloon catheter injury. Vascular endothelial and smooth muscle cell growth was arrested through the ability of p27 CKI to inhibit cyclin-dependent kinases and progression through the G1 phase of the cell cycle. Restenosis is a clinical condition which can be diagnosed and monitored as described in Epstein et al., *JACC* 1994, 23(6):1278 and Landau et al., *Medical Progress* 1994, 330(14):981.

The compositions of the present invention can be used to treat all mammals, in particular humans.

The compositions of the present invention can be administered in combination with immunotherapeutic agents, genetic therapies (e.g. HLA-B7), and proteins (such as cytokines, preferably, Gm-CSF, IL-2 and/or IL-12) Alternatively, the compositions can be administered during adoptive cell transfer therapy.

Having generally described this invention, a further understanding can be obtained by reference to certain specific examples which are provided herein for purposes of illustration only and are not intended to be limiting.

EXAMPLES

Example 1

The effect of p27 overexpression on cell cycle was studied.

Cell Culture and Transfection

1. Plasmids cDNAs expressing human p21, p16, p27, HSV-1 thymidine kinase (tk)), human alkaline (hAP) and human CD2 were introduced in VR1012, an eukaryotic expression vector that contains a cytomegalovirus immediate early gene promoter, enhancer and intron, and a bovine growth hormone polyadenylation signal. A plasmid expressing HIV-1 Vpr under the control of a CMV immediate early gene promoter and a SV40 polyadenylation signal was provided by Dr. E. Cohen (University of Montreal, Canada). (see Yang et al., *Nat. Med.* 1995, 1:1052 and Ohno et al., *Science* 1994, 265:781).

A dicistronic construct expressing p27 and tk (pCMVp27CITEtk) was made by inserting the EcoRI-NcoI fragment from pCITE-1 (Novagen, Wis.) between a XbaI site located immediately downstream from the p27 coding sequence and a NcoI site encompassing the initiator codon of the tk gene. This EcoRI-NcoI fragment ("CITE") contains a copy of the encephalomyocarditis virus (EMC) RNA 5' non-coding region, which functions as an internal entry point for initiation of translation by eukaryotic ribosomes. As a control for p27 activity, a vector containing the p27 coding region but in reverse orientation respective to the CMV promoter, was constructed in a similar way. To reduce the size of the expression cassette, the SacII-EcorV fragment containing the CMV intron was deleted in both vectors.

A fusion protein between p27 and tk was made by deleting a AatII-NcoI fragment from pCMVp27CITEtk, giving rise to plasmid pCMVp27tk. The resulting protein was deleted for the last four amino acids of p27 (RRQT; SEQ ID NO:3) and an additional serine residue was inserted in front of the first methionine of the thymidine kinase.

Mutation of the p27 cdc2 kinase consensus site "TPKK" (SEQ ID NO:4) to "AAGG" (SEQ ID NO:5) was performed using overlapping PCR-based methods, using plasmid pCMVp27 citetk as a template. On one side, sequences corresponding to nt. 186 to nt. 576 from the start of the p27 coding region were amplified using the oligonucleotides #26 (5'-CGATTTTCAGAATCACAAACCCC-3') (SEQ ID NO: 6) and #24(5'-GCCAGGCCCCCGGCCG-CCTGCTCCACAGAACC-3') (SEQ ID NO: 7) as primers. On the other side, sequences corresponding to nucleotide 554 from the start of the p27 coding region to the BglI site located in the downstream CITE sequences were amplified using the oligonucleotides # 23 (5'-GAGCAGGCGGCCGGGGGGCCTGGCCTCAGAAG-3') (SEQ ID NO: 9) and #27 (5'-TTTGGCCGCAGA-GGCACCTGT-3') (SEQ ID NO:9). Mutations in oligonucleotides #23 and #24 differ from the wild type in the relevant positions. Both PCR products were amplified in a single reaction using oligos #26 and #27 as primers, with 6 cycles (94° C., 15 sec/45° C., 30 sec/72° C., 45 sec) followed by 30 cycles (94° C., 15 sec/65° C., 30 sec/72° C., 45 sec). The resulting DNA fragment was digested with SacII and XbaI, and inserted into pCMVp27CITEtk to replace the corresponding fragment. The integrity of the sequences was verified by sequencing.

A fusion between the N-terminal part of the p27 coding region and the sequences encoding the thymidine kinase was created by deleting the SacII-NcoI fragment from pCMVp27citetk, giving rise to plasmid pCMVp27SNtk. Similarly, pCMVp27SFtk and pCMVp27NFtk were constructed by deleting the SacII-FspI and NarI-FspI fragments, respectively, from pCMVp27tk.

Introduction of the N-terminal part of p21 downstream of the cyclin-cdk2 binding domain of p27 was performed by ligating a NcoI-HindIII fragment from plasmid VR1012-p21N, between the SacII and FspI sites of pCMVp27tk, giving rise to plasmid pCMVp27Sp21Ftk. VR1012-p21N contains a copy of the sequences coding for the first 75 amino amino acids of p21. Similarly, pCMVp27Np21Ftk was constructed by inserting the same NcoI-HindIII fragment between the NarI and FspI sites of pCMVp27tk.

2. 293 Cells Transfections and FACS Analysis 293 cells were cultured in Dulbecco's modified Eagles's medium supplemented with 10% fetal calf serum at 37° C. and 5% $CO_2$ Cells ($2 \times 10^6$) seeded the previous day in 10-cm diameter culture dishes were transfected with 15 mg of plasmid DNA using the $CaPO_4$ method as described previously. For cell cycle analysis, 293 cells were typically transfected with 3 μg of CD2-expressing plasmid of 12 mg of cell cycle inhibitor-expressing plasmid.

One day after transfection, cells were detached from the tissue culture dish with 2 mMEDTA-containing PBS. Cell clusters were disrupted by pipeting the cell suspension in and out a few times, and $10^6$ cells were reseeded on a 15-cm diameter dish. The next day cells were harvested and tested simultaneously for cell surface CD2 and DNA content by flow cytometry, as previously described (Shrid et al., 1991). Briefly, $10^6$ cells were incubated with 50 ml of anti-CD2 mouse hybridoma supernatant (ATCC No HB222) for 20 min on ice. The cells were then washed twice with 1 ml of PBS-2% fetal calf serum and incubated with 0.2 mg of fluorescein isothiocyanate (FITC)-conjugated sheep anti-mouse immunoglobulin in 50 ml of PBS-2% fetal calf serum for 20 min on ice. The cells were washed with 1 ml PBS-2% fetal calf serum, and fixed in 0.25% paraformaldehyde-PBS for 1 h on ice. The fixed cells were permeabilized with 0.2% tween 20-PBS for 15 min at 37° C. The cells were washed again with 1 ml PBS-2% fetal calf serum, and incubated for 1 hour at 37° C. in 1 ml PBS containing 30 mg of propidium iodide and 2 units DNAse-free RNAse (Boerhinger Mannheim) per ml. Fluorescence was analyzed on a FAC-SCAN (Becton Dickinson) flow cytometer. Data represent at least 10 000 events, corresponding to the cells expressing the highest CD2 levels. The DNA profiles were analyzed using ModFit LT software (Verity Software House, Inc.).

3. Bystander Assay

Renca cells were cultured in RPMI medium supplemented with 10% fetal calf serum at 37° C. and 5% $CO_2$. Cells were cultured in 10-cm diameter dishes until they reach 90% confluency and then transfected with 25 mg DNA complexed with 100 mg Lipfectamine (Gibco BRL). For bystander experiments, Renca cells were typically transfected with 5 mg of CD2-expressing plasmid and 20 mg of tk-expressing plasmid.

One day after transfection, cells were harvested and diluted with increasing amounts of untransfected cells. $10^4$ cells were seeded per well in a 96-well plate and incubated 6 hours at 37° C. to permit cell adherence to the plate. The media was then changed to fresh media containing 5 mM GCV. Cultures were terminated at 5 days, and cell proliferation was measured using a colorimetric assay. To determine transfection efficiencies, 0.5 $10^6$ cells were seeded in a 10 cm-diameter culture dish, and incubated another day at 37° C., Cells were then harvested and analyzed by FACS for CD2 expression as described above.

Results

1. Overexpression of p27 Arrests Various Cells Lines More Strongly than p21 p16 or Vpr.

Four cyclin-depend kinase inhibitors (p21, p27, p16 and Vpr) were tested in 293 cells, an adenovirus-transformed embryonic kidney cell line. Vectors expressing p21, p27, p16, Vpr or hAP under the control of CMV enhancer/promoter were transfected into 293 cells together with a CD2 expressing plasmid. All inhibitors were expressed under the control of the CMV promoter in order to obtain similar mRNA levels from all constructs. After two days of expression, cells were harvested and stained simultaneously with an anti-CD2 antibody and propidium iodide. Upon cotransfection of these plasmids with another vector expressing the cell surface marker CD2 (CMV-CD2), cells were sorted by flow cytometry and analyzed for DNA content.

In p21- and p27-transfected 293 cells, the proportion of cells in G1 phase was 58% and 76% respectively, compared to 27% for the control.

2. Optimization of p27-Mediated G1 Arrest

A vector coexpressing p27 and TK was constructed. Both coding sequences were inserted in a single transcription unit in order to reduce the size of the vector and to avoid competition between two adjacent promoters. A small size vector is indeed an important feature for an optimal gene transfer, especially if it has to be transferred into current-generation adenoviral vectors, which have a capacity of 4.5 kbp when only the E1 region is deleted. p27 was inserted downstream from the CMV promoter, and followed by an Encephalomyocarditis virus (EMCV) internal ribosome entry site (CITE), the TK coding sequence and a polyadenylation signal from a bovine growth hormone gene, giving rise to CMVp27CITETK.

To test the ability of this vector to arrest the cell cycle in G1, 293 cells were transfected with a mixture of CMVp27CITETK and CMVCD2 as an internal control. Two days after transfection, cells were analyzed simultaneously for DNA content and CD2 expression. All plasmids had been transfected with similar efficiencies since the percentages of CD2-expressing cells were comparable for all samples.

Mutation of the cdc2 kinase consensus site TPKK (SEQ ID NO: 4) into AAGG (SEQ ID NO: 5) moderately increases p27 activity. Internal deletions inside the p27 coding region also increases p27 activity. Fusion of the N-terminal domains of p21 and p27 does not increase cell cycle arrest in G1.

Example 2

To determine whether CKI expression is associated with arterial repair, Western blot analysis was performed on normal and injured porcine arteries. Porcine arterial injury is a well-studied animal model of human vascular disease in which following vascular injury, intimal smooth muscle cell proliferation begins at 1–2 days, increases rapidly and peaks at 15–18% of intimal cells at 7 days, and declines to 1–2% at 14 days.

Porcine femoral arteries were injured with a balloon catheter (C. R. Bard, Billerica, Mass.) at a pressure of 500 mm Hg for 5 minutes and isolated at day 1, 4, 7, 14, 21, 60 after injury. Uninjured porcine femoral arteries and porcine coronary arteries were isolated as well. The number of specimens ranged from 2 to 4 for the different time points. Uninjured human coronary arteries were obtained from patients undergoing heart transplantation. Eight specimens with diffuse intimal thickening, seven specimens with beginning atherosclerosis, and twenty specimens with advanced atherosclerosis were obtained. All the specimens were fixed in formalin, embedded in paraffin, placed onto polylysine coated slides, deparaffinized in three changes of xylene and rehydrated in 100%, 95%, 75% ethyl alcohol.

Immunohistochemical studies were performed with antibodies to p27 (1:100 dilution, mouse monoclonal antibody, Pharmingen), p21 (1:500 dilution, rabbit polyclonal antibody, Santa Cruz), p16 (1:5000 dilution, rabbit polyclonal antibody, Santa Cruz), smooth muscle α-actin (1:500 dilution, mouse monoclonal antibody, Boehringer), CD68 (1:100 dilution, mouse monoclonal antibody, DAKO). Slides were incubated in 0.3% hydrogen peroxide for 30 minutes to exhaust endogenous peroxidase activity. Primary antibodies were diluted in PBS with 1% BSA and applied to the slides for 12 hours at 4°. After several washes biotinylated secondary horse anti-mouse IgG or horse anti-rabbit IgG (1:400 dilution, ZYMED) was applied to the slides for 30 minutes at room temperature. The specimens were developed with an alkaline phosphatase reagent (Vector Laboratories) for 30 minutes at room temperature yielding a red reaction product and then counterstained with methyl green.

L293 cells were transfected with RcCMVp16, RcCMVp2 I, RcCMVp27, RcCMVβ-galactosidase or RcCMV control plasmid by the calcium phosphate method. The cells were washed in PBS at 48 hours after transfection and pellets were prepared for iunmunohistochemistry. Antibodies to p27, p21 and p16 were tested on cells transfected with the respective cDNA as well as on cells transfected with the control plasmid. Staining of cells transfected with the respective cDNA was comparable to the transfection efficiency as determined by β-galactosidase expression while cells transfected with the control plasmid were not stained. Mouse IgG was used as negative control for the monoclonal antibodies and rabbit serum for the polyclonal antibodies. These control primary antibodies did not lead to staining of transfected cells nor arterial specimens. Antibodies were also preabsorbed with lysate from L293 cells transfected with one of the cyclin-dependent kinase inhibitor cDNAs or with the control plasmid. The positive lysates abolished staining of transfected cells and arterial specimens by the respective antibody while the control lysate did not.

A well characterized arterial specimen from previous studies served as positive control for the smooth muscle α-actin antibody and human tonsil for the CD68 antibody. Double labeling immunohistochemistry for cyclin-dependent kinase inhibitors plus smooth muscle α-actin or cyclin-dependent kinase inhibitors plus CD68 was performed according to the Vector Laboratories protocol. A red reaction product was chosen for p21 and p27, a blue reaction product for smooth muscle α-actin and CD68, and the methyl green counter stain was performed as for the single labeling studies.

Expression of p16, p21 and p27 was quantified for intima, media and adventitia separately. An average value was determined for each time point by adding the score obtained from individual specimens and dividing the sum by the number of specimens. Intimal and medial areas were measured by digital planimetry (Image One System, Universal Imaging, West Chester, Pa.) and intima to media ratios were calculated.

Western blot of porcine cell lines from normal and injured arteries were performed. The neointima was fully formed at 21 days. Constitutive p27 expression was detected in quiescent arteries, expression decreased at 1 day, while p27 expression was observed 7 days later increasing at 21 days. The time course and cell type expressing p27 was investigated by immunohistochemistry. Compared to p21 expression, p27 was expressed in smooth muscle cells of normal arterial intima and media, and in the adventitia. After injury, p27 protein was detected in <1% of these cells and remained low until 7 days when expression was detected in developing neointima. When the neointima was fully formed (21 days), p27 expression was pronounced in the lower regions of the intima, adjacent to the internal elastic lamina.

The expression of cyclin-dependent kinase inhibitors after arterial injury was also measured. p27 was expressed at high level in uninjured arteries, at low level at day 7 after injury and at high level again at day 21 after injury. Expression of p21 did not vary much during this time. Expression of p16 could not be detected in uninjured arteries, was present at 4 days after injury and was not present anymore at later time points.

p27 was expressed at high level in quiescent arteries and from 21 days after injury onwards, while expression markedly declined during the first 14 days after injury. p21 was expressed in quiescent arteries and expression did not vary considerably after injury. p16 could not be detected except at day 1 and 4 after injury. Similar changes in expression were observed for the intima and for the media.

In contrast to p21, p27 protein was prominent in all layers of the arteries 60 days later at a time when the repair process had been completed. The expression of p27 was inversely correlated with cell proliferation, previously determined by BrdC incorporation. In contrast, p16 expression was not detected in quiescent or injured arteries by Western analysis or immunohistochemistry.

Example 3

Infection of VSMC by recombinant adenovirus was studied.

Porcine and human VSMC and HeLa cells were infected with the β-galactosidase adenovirus at moi 300 pfu/cell. Only 12±3% of porcine and 10±2% of human VSMC were staining positive for β-galactosidase. This percentage increased to 40±4% for porcine and 35±4% for human VSMC at moi 1500 pfu/cell.

In contrast, 92±1% of HeLa cells were positive for β-galactosidase at moi 300 pfu/cell and all the cells at 1500 pfu/cell. Similarly, 76±3% of A549 cells were positive at moi 300 pfu/cell and all the cells at 1500 pfu/cell. Very high multiplicities of infection were necessary for effective infection of VSMC (95±2% of porcine and 95±1% of human cells positive for β-galactosidase at moi 15000 pfu/cell).

Example 4

The effects of p27, p21, and p16 in VSMC proliferation in vitro were investigated. Adenoviral vectors encoding p27, p21, and p16 were constructed and the effects of CKI expression on VSMC growth were examined. Control experiments were performed with an adenoviral vector lacking an insert in the E1 region (ADV ΔE1) and with no virus.

Effect of cyclin-dependent kinase inhibitors on proliferation of porcine aortic vascular smooth muscle cells. 10000 cells per group were infected with p16 or p21 or p27 adenovirus at a moi of 5000 pfu/cell (right panel) or 10000 pfu/cell (left panel). Cells infected with control virus (ΔE1) as well as noninfected cells served as negative control. Cell number was determined every other day for up to 8 days using a hematocytometer.

The cDNAs for human p27, p21 and p16 were ligated into the RcCMV (Invitrogen) plasmid and sequenced by the dideoxy chain termination method. Recombinant adenoviruses were constructed by cotransfection of truncated viral DNA (Ad5 sub360) and a plasmid harboring one of the cDNAs flanked by adenoviral map unit 0–1 for viral propagation as well as map unit 9–16 for homologous recombination. The resulting adenoviruses had a deletion in the E1 and E3 region and contained one of the cDNAs under control of the cytomegalovirus promoter and the bovine growth hormone polyadenylation site. Individual plaques were isolated and recombinant viruses were subjected to at least two rounds of plaque purification. Viruses were purified in a double-banded cesium chloride gradient and analyzed for the presence of the transgene by Southern blot analysis, Western blot analysis, and inhibition of proliferation of several cell lines. A β-galactosidase expressing virus and a virus deleted in E1 but lacking a transgene (ΔE1) were purified in an identical manner. The titer of purified viruses was determined by plaque assay on 293 cells using an adsorption time of 24 hours and counting the number of plaques on day 12 after infection. Titers ranged from $5 \times 10^{10}$ to $2 \times 10^{11}$ pfu/ml for all preparations. The titer of wild type virus in the purified preparations was determined by plaque assay on A549 cells using the same conditions as for 293 cells and was below 1 in $10^9$ pfu for all preparations.

Porcine aortic vascular smooth muscle cells were isolated by the explant method and maintained in DMEM supplemented with 20% FCS. Human aortic vascular smooth muscle cells were obtained from Clonetics and cultured in M199 supplemented with 20% FCS. Vascular smooth muscle cells (VSMC) were used for experiments between passage number 2 and 10. 293 cells, A549 cells and HeLa cells were obtained from ATCC and cultured as recommended. Infectibility of A549 cells, HeLa cells and VSMC was analyzed using the β-galactosidase adenovirus at increasing multiplicity of infection (moi) ranging from 300 to 15000 pfu/cell. β-galactosidase expression was analyzed at 24 hours after infection by fixing the cells in 1.25% glutaraldehyde and staining with X-gal for 1 h at 37°. The percentage of infected cells was determined by counting the stained cells as well as the total number of cells on 5 random microscopic fields at 200× magnification. Cells infected with ΔE1 virus as well as noninfected cells were used as negative controls for all these experiments.

To determine in which phase of the cell cycle the growth arrest was present, smooth muscle cells overexpressing p27, p21 or p16 were stained with propidium iodine and analyzed by flow cytometry. Overexpression of p27 and p21 resulted in inhibition of cell growth following transduction and maintenance in 20% FCS. In contrast, overexpression of p16 produced partial inhibition of smooth muscle proliferation. Equivalent expression of the CKIs was present so that differences in growth inhibition were qualitative, not quantitative.

Example 5

Effect of cyclin-dependent kinase inhibitors on cell cycle distribution of porcine aortic vascular smooth muscle cells was investigated. Cells were infected with p16 or p21 or p27 adenovirus at a moi of 5000 pfu/cell or 10000 pfu/cell. Cells infected with control virus (ΔE1) as well as noninfected cells served as negative control. Cell cycle distribution was determined at 48 hours after infection by staining with propidium iodide.

For analysis of proliferation VSMC were seeded at a density of 10000 cells per 35-mm-dish and cultured for 24 hours prior to adenoviral infection with a moi of 5000 or 10000 pfu/cell. Upon infection the cells were maintained in the usual medium and cell number was determined every other day for up to 8 days using a hematocytometer. To examine cell cycle distribution and cell size VSMC were seeded at a density of 250000 cells per 15-cm-dish and cultured for 24 hours prior to adenoviral infection with a moi of 5000 or 10000 pfu/cell. 24 h after infection the cells were split at a ratio of 1:2 and cultured for an additional 24 h which resulted in 40 to 60% confluency at the time of analysis. Cell cycle distribution was examined after fixation in 2% paraformaldehyde, permeabilisation in 0.2% Tween-20, staining with propidium iodide at a final concentration of 30 μg/ml and analysis of DNA content at excitation 493 nm using a flow cytometer (FACSCAN, Becton Dickinson). Cell size was determined by flow cytometer using forward angle scatter as well as geometric means were calculated with a cytometer software (CELLQUEST Becton Dickinson). Cells infected with ΔE1 virus as well as non-infected cells were used as negative controls for all these experiments of this example.

Overexpression of p27, p21 and p16 promoted G1 arrest compared to non-transduced cells or cells transduced with ADV-ΔE1 vectors. Cell size in p27, p21 and p16 transduced cells was larger compared with control cells determined by flow cytometric analysis of cell size.

Example 6

The effect of growth factors on cell cycle distribution of porcine VSMC was investigated. Cells described in Example 5 were cultured in the presence of bovine serum albumin or fetal calf serum. When cells were cultured in the presence of 0.2% bovine serum albumin (BSA), the population arrested in G1. In the presence of 20% fetal calf serum (FCS), the cells were proliferating as indicated by the higher number of cells in S and G2/M phases.

Example 7

The effect of growth factors on p27 protein level and functional consequences was investigated. Primary VSMC cultured in the presence of 0.2% bovine serum albumin (BSA) (left panel) were arrested in G1 S phase. In the presence of 20% A fetal calf serum (FCS), VSMC were stimulated to proliferate, and the number of G1/IS phase arrested cells decreased substantially. Primary porcine aortic VSMC were isolated by an explanation method (Ohno et al., *Science* 1994, 265:781) and maintained in M199 containing 20% FCS. Twenty four hours prior to cell cycle analysis, VSMC were carried in M199 with 0.2% BSA or DMEM with 20% FCS. For analysis of cell cycle, cells were harvested 24 hours later, washed and phosphate-buffered saline (PBS) twice, and fixed in 2% paraformaldehyde for 60 min and permabilized in 0.2% Tween-20. The cells were treated with 1 unit of Dnase-free Rnase in 1 ml of PBS for 30 nm at 37° C., resuspended in 0.03 mg/ml propidium iodide, and analyzed by flow cytometry using a FACSCAN model (Becton Dickinson).

The p27 protein level was higher in the presence of 0.2% bovine serum albumin (BSA) than fetal calf serum (FCS) indicating an inverse relationship of p27 protein level and growth factor concentration, as determined by Western blot analysis. In contrast, cdk2 protein level did not change much in the presence of FCS, as determined by Western blot analysis. p27 in complex with cdk2 kinase changed similar to total p27 level in the presence of BSA versus FCS. In line with this observation cdk2 kinase activity was lower in BSA as compared to FCS.

Example 8

The expression patterns of p27, p21 and p16 in human blood vessels were examined in order to determine whether this CKI model of vascular smooth muscle cell growth arrest was applicable to human vascular disease.

Forty specimens of aorta and coronary arteries were obtained from hearts removed from 25 patients (18 men and 7 women, ages 21–67) undergoing heart transplantation. These segments were classified into three groups by classic histological criteria: diffuse intimal hyperplasia, characteristic of aging human arteries without clinical or morphological evidence of atherosclerosis; early atherosclerosis, characterized by some lipid deposition and focal necrosis; and advanced atherosclerosis, with a fibrous cap, necrotic core, lipid deposition, focal necrosis and calcification. Tissues were snap frozen in liquid nitrogen for Western blot analysis and stored at −70° C., or fixed in 10% buffered-formalin for 4 hours, followed by 70% ethanol for 18 hours, and paraffin embedded. Sections (6 μm thick) were placed onto poly-L-lysine coated slides and immunostaining was performed. Both p27 and p21 were expressed at all stages of atherogenesis while p16 could not be detected in any of the specimens.

Atherosclerotic human coronary arteries were double-labeled with anti-p27 or anti-p21 antibodies and a smooth muscle cell marker α-action p27 and p21 expression in the intima colocalized with smooth muscle cells. Double label immunostaining was performed with p27 and p21 antibodies and a smooth muscle cell marker, α-actin, using standard techniques. A red reaction product was chosen for p21 and p27, a blue reaction product for smooth muscle α-actin, and the methyl green counter stain was performed. Smooth muscle α-actin positive cells (blue) express p21 (red) as well as p27 (red).

p27 as well as p21 were present in the intima, media and adventitia, while p16 could not be detected in these arteries. Expression of p27 and p21 was present in arteries with diffuse intimal hyperplasia as well as in atherosclerotic specimens. Expression of p27 and p21 was associated with α-actin positive cells and CD 68 positive cells confirming their identity as smooth muscle cells and macrophages. These CKIs were not associated with cells expressing the cell proliferation marker Ki67. These findings indicate that p27 and p21 are expressed in human arteries with diffuse intimal hyperplasia as well as during atherogenesis. In contrast, p16 seems to be expressed at very low level (see Table 1).

TABLE 1

Expression of p27 in human coronary arteries

| Branch | LAD | LCX | RCA |
|---|---|---|---|
| Specimens | 0 | 10 | 16 |
| Intima | 7 | 9 | 13 |
| Media | 7 | 9 | 13 |
| Adventitia | 8 | 9 | 13 |

Example 9

Expression pattern of p27, p21 and p16 was examined in human coronary arteries with diffuse intimal thickening, beginning atherogenesis and advanced atherogenesis.

Transit through G1 of the cell cycle and entry into S phase requires the binding and activation of cyclin/cyclin-dependent kinase (CDK) complexes, predominantly cyclin D-cdk4 and cyclin E-cdk2. The cyclin-dependent kinase inhibitors (CKIs) p27 and p21 inhibit cyclin-cdk acitivty, resulting in G1/S growth arrest. To determine whatever expression of these CKIs inhibits vsmc proliferation, porcine vsmc were transfected with adenoviral vectors expressing p27, p21 or p16 or a control virus AdΔE1 Expression of p27 and p21 resulted in complete inhibition of vsmc proliferation compared to AdΔE1 transfected cells (p<0.01) while p16 expression induced a partial inhibition of vsmc growth (63%) compared to controls). Propidium iodide staining an FACS analysis demonstrated G1 arrest. Kinase assays and immunoprecipitation studies demonstrated inhibition of cdk2 activity by p27 and p21 but not p16. To study the effects of CKI expresion in vivo. Adenoviral gene transfer of p27 and p16 was performed in balloon injured porcine arteries. Seven days following gene transfer, intimal vsmc proliferation was reduced in p27 arteries compared with p16 and AdΔE1 control arteries (p<0.05). This reduction in proliferation was associated with an inhibition of intimal area in p27 arteries (0.5±0.06 mm2) compared with p16 (1.13±0.09 m2) and AdΔE1 control arteries (0.98±0.8 mm2) (p<0.5). Thus, the KIP/CIP CKIs p27 and p21 negatively regulate vsmc proliferation compared to the INK CKI p16. These studies suggest differential roles of KIP/CIP and INK CKIs in regulating G1 arrest in the cell cycle in vsmcs.

The references cited throughout the detailed description are incorporated herein by reference. Having now fully described the invention, it will be apparent to one of ordinary skill in the art that many changes and modifications can be made thereto without departing from the spirit or scope of the invention as set forth herein.

What is claimed is:

1. A combination for treating a vascular proliferative disease in a patient comprising a nucleic acid encoding a single cyclin-dependent kinase inhibitor contained in a balloon catheter, wherein the cyclin-dependent kinase inhibitor is p27.

2. The combination of claim 1, wherein the balloon catheter is a single balloon catheter.

3. The combination of claim 1, wherein the balloon catheter is a double balloon catheter.

4. The combination of claim 1, wherein the nucleic acid is an expression vector.

5. The combination of claim 1, wherein a viral particle contains the nucleic acid.

6. The combination of claim 1, further comprising a liposome.

7. The combination of claim 1, further comprising a nucleic acid encoding a cytotoxic agent.

8. The combination of claim 7, wherein the cytotoxic agent is selected from the group consisting of thymidine kinase, cytosine kinase, cytosine deaminase, and nitric oxide synthetase.

9. The combination of claim 7, wherein the nucleic acid encoding p27 and the nucleic acid encoding the cytotoxic agent are operatively linked.

10. The combination of claim 7, wherein the nucleic acid encoding p27 and the nucleic acid encoding the cytotoxic agent form a dicistronic construct.

11. The combination of claim 8, wherein the cytotoxic agent is thymidine kinase.

12. The combination of claim 9, wherein the nucleic acid encoding p27 and the nucleic acid encoding the cytotoxic agent are operatively linked such that they encode a fusion protein.

13. The combination of claim 12, wherein the fusion protein is a p27-thymidine kinase fusion protein.

* * * * *